United States Patent [19]

Allison

[11] Patent Number: 5,650,167
[45] Date of Patent: Jul. 22, 1997

[54] METHOD AND COMPOSITION FOR TREATING HEPATITIS B

[75] Inventor: Anthony C. Allison, Belmont, Calif.

[73] Assignee: DAWA Incorporated, Belmont, Calif.

[21] Appl. No.: 559,548

[22] Filed: Nov. 16, 1995

[51] Int. Cl.$^6$ .................................................. A61K 9/20
[52] U.S. Cl. .................... 424/451; 424/464; 514/510; 514/577; 514/894
[58] Field of Search ................... 424/422, 451, 424/464; 514/894, 510, 577

[56] References Cited

U.S. PATENT DOCUMENTS 4,328,309  5/1982  Chalmers.

FOREIGN PATENT DOCUMENTS 4117854  12/1992  Germany.
91/13627  9/1991  WIPO.

OTHER PUBLICATIONS

Calzada, F., et al., "Friedelanes and Triterpenoid Quinone Methides from *Hippocreatea excelsa*," *Planta Med.* 57:194–195 (1991).
Kumar, V., et al., "21α30-Dihydroxy-D:A-Friedooleanan-3-One from *Salacia reticulata* var. β-Diandra Stem Bark," *Phytochemistry* 29(1):333–335 (1990).
Kutney, J.P., et al., "Studies with Tissue Cultures of the Chinese Herbal Plant, *Tripterygium wilfordii*. Isolation of Metabolites of Interest in Rheumatoid Arthritis, Immunosuppression, and Male Contraceptive Activity," *Can. J. Chem.* 70:1455–1465 (1992).
Moujir, L., et al., "The Relationship Between Structure and Antimicrobial Activity in Quinones from the Celastraceae," *Biochem. System. Ecol.* 18(1):25–28 (1990).
Ngassapa, O., et al., "Quinone-Methide Triterpenes and Salaspermic Acid from *Kokoona ochracea*," *J. Natural Products* 57(1):1–8 (1994).
Sassa, H., et al., "The Triterpene Celastrol as a Very Potent Inhibitor of Lipid Peroxidation in Mitochondria," *Biochem. Biophys. Res. Com.* 172(2):890–897 (1990).
Sassa, H., et al., "Structural Basis of Potent Antiperoxidation Activity of the Triterpene Celastrol in Mitochondria: Effect of Negative Membrane Surface Charge on Lipid Peroxidation," *Free Radical Biol. Medicine* 17(3):201–207 (1994).
Takaishi, Y., et al., "Inhibitory Effects of Dihydroagarofuran Sesquiterpenes on Epstein–Barr Virus Activation," *Cancer Letters* 65:19–26 (1992).
Ujita, K., et al., Inhibitory Effects of Triptogelin A–1 on 12–O–tetradecanoylphorbol–13–acetate–induced Skin Tumor Promotion, *Cancer Letters* 68:129–133 (1993).
Li, X.–Y. Anti–inflammatory and Immunosuppressive Components of *Tripterygium wilfordii* Hook F. *Int. J. Immunotherapy* IX(3):181–187 (1993).

Primary Examiner—Raj Bawa
Attorney, Agent, or Firm—Vincent M. Powers

[57] ABSTRACT

Disclosed is a method of inhibiting hepatitis B infection by administering a therapeutically effective amount of a compound having the formula (Formula 1):

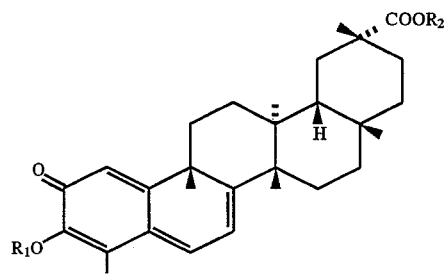

wherein R1 is selected from the group consisting of H, lower alkanoyl, lower arylalkylacyl, arylacyl, and C-1-linked saccharide, and R2 is separately selected from the group consisting of H, lower alkyl, lower arylalkyl, aryl, and C-1-linked saccharide. The compounds may also be used to treat other conditions, such as inflammatory bowel disease, autoimmune diseases, transplant rejection, septic shock, and for protection against irradiation damage. Novel celastrol derivatives are also disclosed.

6 Claims, 3 Drawing Sheets

METHOD AND COMPOSITION FOR TREATING HEPATITIS B

FIELD OF THE INVENTION

The present invention relates to a composition and method for treatment of hepatitis B, and to compositions and methods for immunosuppression and various other therapeutic indications.

REFERENCES

Aprahamian et al., *J. Biomed. Mat. Res.* 21:965–977 (1986).

Belshe, R. B., *Textbook of Human Virology*, 2nd Ed., Mosby Year Book, Inc., St. Louis, Mo., pp. 719–748 (1991).

Dumont, F. J., et al. *Handbook of Experimental Immunology*, 5th Edition, Blackwell Science, Boston, Mass., 1995.

Ding, A. H., et al., *J. Immunol.* 141:2407 (1988).

Emmanuel et al., *Stain. Tech.* 62:401–409 (1987).

Friendenstein et al., *Exp. Hematol.* 10:217–227 (1982).

Kutney, *Can. J. Chem.* 59:2677 (1981).

Marion et al., *Hepatology* 7:724 (1987).

Pugh, J., et al., *J. Virol.* 62:3513 (1988).

Price, et al., *Proc. Nat'l. Acad. Sci. USA* 86:8451 (1989).

Sambrook, J., et al., *Molecular Cloning: A Laboratory Manual*, 2nd Edition (Cold Spring Harbor Laboratory Press, Cold Spring Harbor, N.Y.) (1989).

Siddiqui, A., et al., *J. Virol.* 38:393–397 (1981).

Uchida et al., *J. Biomed. Mat. Res.* 21:1–10 (1987).

Wilson et al., eds., *Harrison's Principles of Internal Medicine*, 12th Ed. McGraw-Hill, Inc., N.Y., chap. 252–253 (1991).

Zhang, W., et al., *Acta Pharm. Sin.* 21:592 (1986a).

Zhang, L., et al., *Zhongguo Yaoli Xuebao* 7:85 (1986b).

BACKGROUND OF THE INVENTION

Varieties of chronic hepatitis are a significant cause of morbidity and mortality. The pathogenesis of hepatitis involves death of liver cells (hepatocytes) and fibrosis (cirrhosis). Chronic hepatitis can be caused by persistent infection with a virus such as hepatitis B virus (HBV) or hepatitis C virus (HCV), and may also involve autoimmune processes. The involvement of immunopathology in some forms of hepatitis has led to the treatment of chronic hepatitis conditions with glucocorticoids and immunosuppressive drugs, including azathioprine, cyclosporine and methotrexate. However, these compounds have undesirable side effects and are limited in therapeutic efficacy.

Chronic HBV infections have been treated with interferon. However, this treatment produces limiting side effects and induces prolonged suppression of HBV replication in only about 25% of patients. Nucleoside analogs have also been used to suppress the replication of HBV, but can have severe side effects. In the case of treatment with glucocorticoids, it has been found that the inhibition of the immune response can lead to an elevated level of replication of HBV, augmenting the spread of virus and increasing the risk of developing hepatocellular carcinoma. Moreover, prolonged use of glucocorticoids is associated with metabolic bone disease.

Accordingly, there is need for better therapeutic drugs for treating HBV infection. Ideally, such a drug will be effective to inhibit viral replication in hepatocytes. In addition, the drug should be amenable to delivery by a variety of routes, including oral administration. The drug should also have a long shelf life to allow for shipping and storage. It would also be desirable for such a drug to have anti-replicative activity as well as an ability to inhibit the immune response.

SUMMARY OF THE INVENTION

The present invention includes, in one aspect, a method of inhibiting hepatitis B infection in a mammalian subject, and particularly a human subject, wherein the subject is administered a therapeutically effective amount of a compound having the following structural formula (Formula 1):

wherein R1 is selected from the group consisting of H, lower alkanoyl, lower arylalkylacyl, arylacyl, and C-1-linked saccharide, and R2 is separately selected from the group consisting of H, lower alkyl, lower arylalkyl, aryl, and C-1-linked saccharide.

In one embodiment, the compound administered is selected from the group consisting of celastrol (R1 and R2=H), pristimerin (R1=H, and R2=methyl), and acetyl-celastrol (R1=acetyl, and R2=H). In another embodiment, the compound is administered in a form wherein R1 and R2 are independently selected from the non-hydrogen substituents noted above. In a preferred embodiment, R1 is acetyl and R2 is selected from the group consisting of methyl and ethyl. According to one general embodiment, the compound is administered orally.

In another aspect, the invention includes novel diester compounds having the structural formula shown above (designated herein as Formula 2), wherein R1 is a non-hydrogen substituent selected from the group consisting of lower alkanoyl, lower arylalkylacyl, arylacyl, and C-1-linked saccharide, and R2 is separately a non-hydrogen substituent selected from the group consisting of lower alkyl, lower arylalkyl, and aryl. In one preferred embodiment, R1 is acetyl and R2 is methyl or ethyl.

In addition to being useful in treating hepatitis B infection, the compounds in accordance with the invention may be used in treating a variety of other conditions, such as inflammatory diseases of the bowel, particularly Crohn's disease and ulcerative colitis; autoimmune diseases including nephritis, rheumatoid arthritis, systemic lupus erythematosus, autoimmune diabetes mellitus and multiple sclerosis; organ and cellular transplant rejection; graft-versus-host disease; septic and traumatic shock; and in protecting selected tissues from damage due to irradiation of adjacent tissues. The compounds may also be co-administered with oxidative drugs such as anthracyclines, as a means of protecting the intestinal tract from oxidative damage caused by the latter class of drugs, or with oxidative drugs such as bleomycins to reduce oxidative side effects and fibrosis in the lungs.

Accordingly, the invention also includes methods of treating the conditions set forth in the preceding paragraph, by administering to a subject a therapeutically effective amount of a compound in accordance with Formula 2.

In yet another aspect, the invention includes a method of inhibiting fibrogenesis in the peritoneal or pelvic cavity of a mammalian subject. In the method, a subject in need of such treatment is administered a therapeutically effective amount of a compound in accordance with Formula 2, wherein the drug is administered by injection into the peritoneal or pelvic cavity.

These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise.

"Celastrol" refers to a compound having the structure shown in Formula 1 above, where R1 and R2 are H. Alternative names used in the art for celastrol include "tripterine" and "tripterin".

"Acetylcelastrol" refers to a compound of Formula 1 wherein R1 is acetyl and R2 is H. Alternative names include "acetyltripterine", "acetyltripterin", "tripterin acetate", and "celastrol monoacetate".

"Pristimerin" refers to a compound of Formula 1 wherein R1 is H and R2 is methyl. An alternative name for this compound is "celastrol methyl ester."

"Celastrol diester" refers to compounds of Formula 1 wherein R1 is a non-hydrogen substituent selected from the group consisting of lower alkanoyl, lower arylalkylacyl, arylacyl, and C-1-linked saccharide, and R2 is separately a non-hydrogen substituent selected from the group consisting of lower alkyl, lower arylalkyl, and aryl.

A compound that is "substantially pure" refers to a compound having a purity of greater than 95% on a weight basis with respect to impurities stemming from synthesis of the compound or isolation of the compound from a natural (e.g. plant) source.

"Method of treating hepatitis" encompasses treatment of a mammalian subject, particularly a human subject, and includes (i) arresting the development of clinical symptoms of the disease, (ii) bringing about a regression in the clinical symptoms of the disease, and/or (iii) prophylactic treatment for preventing the onset of hepatitis infection, e.g., following liver transplantation from an HBV carrier.

The term "mammal" is intended to have its standard meaning, and encompasses humans, dogs, cats, sheep, and cows, for example.

"HBV" refers to hepatitis B virus.

"Acyl" refers to a radical having the form —C(O)R, where R is an alkyl, aryl, or an arylalkyl group.

"Alkyl" refers to a fully saturated monovalent radical containing carbon and hydrogen, and which may be cyclic, branched or a straight chain. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl, and cyclohexyl.

"Lower alkyl" refers to an alkyl radical of one to six carbon atoms, as exemplified by methyl, ethyl, n-butyl, i-butyl, t-butyl, isoamyl, n-pentyl, and isopentyl.

"Alkylacyl" and "lower alkylacyl" refer to radicals having the form —C(O)R, where R is an alkyl or lower alkyl group.

"Aryl" refers to a substituted or unsubstituted monovalent aromatic radical having a single ring (e.g., benzene) or two condensed rings (e.g., naphthyl). Other examples include heterocyclic aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl.

"Arylacyl" refers to a radical having the form —C(O)R, where R is an aryl group.

"Arylalkylacyl" refers to a radical having the form —C(O)R, where R is an arylalkyl group, i.e., an aryl group linked to a carbonyl carbon by an intervening alkyl group, e.g., phenylmethyl, or phenylpropyl. A "lower arylalkylacyl group" refers to an arylalkylacyl group in which the intervening alkyl group contains one to six carbon atoms.

"C-1-linked saccharide" refers to a furanose or pyranose saccharide (sugar) substituent which is linked to the backbone structure shown in Formula 1 or 2 through the saccharide's 1-carbon (conventional chemical numbering) to form an acetal linkage at the R1 position, or an ester linkage at the R2 position. Exemplary saccharide groups include reducing sugars such as glucose, ribose, arabinose, xylose, mannose, and galactose, each being linked to the structure of Formula 1 or 2 through the C-1 carbon of the saccharide group.

II. Preparation of Compounds

A. Isolation and Synthesis

In one aspect, the invention includes pharmaceutical preparations containing a compound in accordance with Formulas 1 and 2 above, as well as novel compounds in accordance with Formula 2. This section describes methods of preparing such compounds.

Celastrol can be obtained from plants, e.g. *Tripterygium wilfordii* Hook, by methods known in the art (e.g. Kutney et al. (1981); Zhang et al. (1986a,b). Pristimerin can be obtained by reacting celastrol with diazomethane. Acetylcelastrol can be obtained by acylation of celastrol with acetic anhydride in the presence of pyridine.

More generally, compounds of formula 1 above wherein R1 is an acyl group (R1 ester) can be prepared from celastrol (or from an R2 ester formed as discussed below) by standard acylation/esterification procedures. In one approach, esterification is accomplished by reaction of celastrol with the desired acylating agent in the form of an acid anhydride, in the presence of a weak base such as pyridine. For example, treatment of celastrol with acetic anhydride in the presence of pyridine gives an ester in which $R_1$ is $CH_3COO$—. Any mixed anhydride formed at the R2 position, i.e., by reaction of the R2 carboxyl group of celastrol with acid anhydride reagent to produce the corresponding mixed anhydride (R2=C(O)R), can be converted back to the free carboxylic acid (R2=$CO_2H$) by quenching with water, optionally in the presence of base, to produce the desired acylated product (R1=R—C(O)—, and R2=$CO_2H$). The desired product can be purified from the reaction mixture by standard methods, e.g. by extraction and/or silica gel chromatography or high-pressure liquid chromatography.

In a second general approach, esterification at R1 can be achieved by reacting celastrol with an excess of the appropriate carboxylic acid. A catalytic amount of a strong acid, such as sulfuric acid, may be included to hasten esterification. The reaction is continued until the maximum amount of the desired ester product has formed. The product is purified by standard methods as above.

In a third approach, an R1 ester can be formed by reaction of celastrol with the appropriate carboxylic acid chloride or bromide as acylating agent. Typically, a hindered base such as triethylamine or 2,6-di-methylpyridine is included to scavenge the HCl or HBr generated in the reaction. After the reaction is complete, the reaction mixture may be extracted to remove HCl or HBr salts, and the ester product is purified as above.

For preparing esters at the R2 position of the formula 1 compound, celastrol may be reacted with an excess of the appropriate alcohol in the presence of acid or base catalyst to form the desired R2 derivative. For example, treatment of celastrol with excess ethanol in the presence of an acid catalyst affords an R2 ethyl ester in which R2 is ethyl. Other R2 ester derivatives can be produced using appropriate alcohol starting materials. Where a compound in accordance with formula 1 is to be prepared containing ester groups at both the R1 and R2 positions, celastrol will typically be modified at the R1 position first, to produce an R1 ester intermediate, and this intermediate is then esterified at the R2 position as above to afford the desired diester product.

Glycoside derivatives of the compounds of the invention, wherein R1 or R2 is a C-1-linked saccharide, may be prepared by conjugating celastrol, pristimerin, or acetylcelastrol with a reducing sugar such as glucose, ribose, arabinose, xylose, mannose, and galactose, through the C-1 carbon of the sugars.

Glycoside formation may be effected chemically, e.g., by reacting the starting compound with a protected sugar compound in which C-1 has been activated by halogenation for coupling with the hydroxyl or carboxyl groups of celastrol, and the sugar hydroxyls have been blocked by protecting groups (e.g., Friend et al., 1984). Alternatively, glycoside formation may be effected enzymatically using an appropriate glycosyltransferase.

In yet another embodiment, for intravenous or oral administration, the compound in accordance with formula 1 may include a morpholino substituent at the R1 position, e.g., R1=morpholinoethylacyl, to improve serum lifetime of the compound (e.g., Lee et al., *Pharm. Res.* 7:61 (1990)).

The compounds of the invention are preferably prepared in substantially pure form, typically by standard chromatographic methods, prior to formulation in a pharmaceutically acceptable form.

B. Compound Formulations

Administration of the compounds of the invention in an appropriate pharmaceutical form can be carried out via any of a number of accepted modes of administration. Thus, administration can be, for example, oral, nasal, parenteral or topical. The formulations may take the form of solid, semisolid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, antioxidants, and the like. Exemplary formulations are shown in Example 8.

Preferably, the composition will be about 1% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

Preferably, for oral administration, the compositions will take the form of a pill, tablet or capsule. Thus the composition will contain, along with active drug (Formula 1 or 2), a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The compounds of the invention may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline, aqueous dextrose, glycerol, ethanol and the like, to form a solution or suspension. The active compounds may be formulated into a retention enema.

In yet another embodiment, the compounds of the invention are formulated in liposomes using liposome preparation methods known in the art. Preferably, the liposomes are formulated either as small unilamellar vesicles, or as larger vesicles.

If desired, the composition to be administered may also contain minor amounts of non-toxic auxiliary substances such as wetting or emulsifying agents, pH buffering agents, such as, for example, sodium acetate, sorbitan monolaurate, triethanolamine oleate, and antioxidants.

Methods for preparing such dosage forms are known or will be apparent to those skilled in the art; for example, see *Remington's Pharmaceutical Sciences* (1980). The composition to be administered will, in any event, contain a quantity of the pro-drug and/or active compound(s) in a pharmaceutically effective amount for relief of the condition being treated when administered in accordance with the teachings of this invention.

The compounds of the invention may also be introduced in a controlled-release form, for long-term delivery of drug to a selected site over a period of several days or weeks. In this case, the compound of the invention is incorporated into an implantation device or matrix for delayed or controlled release from the device.

The compound is preferably incorporated in a biodegradable material, such as a biodegradable molded article or sponge. Exemplary biodegradable materials include matrices of collagen, polylactic acid-polyglycolic acid, and the like. In preparing the compound in matrix form, the compound may be mixed with matrix precursor, which is then crosslinked by covalent or non-covalent means to form the desired matrix. Alternatively, the compound may be diffused into a preformed matrix. Examples of suitable materials for use as polymeric delivery systems have been described e.g., Aprahamian, 1986; Emmanuel, 1987; Friendenstein, 1982; and Uchida, 1987.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

III. Biological Activity

This section describes studies showing (i) that celastrol is effective to inhibit replication of HBV in hepatoma cells and reduce secretion of HBsAg antigen; (ii) that celastrol inhibits the proliferation of activated mammalian lymphocytes; (iii) that celastrol inhibits the production of the two inflammatory cytokines TNF-$\alpha$ and IL-1$\beta$ in LPS-stimulated human blood monocytes and lung macrophages; (iv) that acetylcelastrol and pristimerin suppress macrophage cytokine production more strongly than celastrol as measured by an acute-phase protein assay; and (v) acetylcelastrol and pristimerin are more effective than celastrol in reducing nitric oxide production in LPS-stimulated alveolar macrophages.

A. Inhibition of HBV Replication

To characterize the ability of the compounds of the invention, as illustrated with celastrol, to inhibit HBV replication, hepatoma cells from the 2.2.15 cell line were used, generated by stable transfection of HepG2 cells (Price et al., 1989).

Figure 1:
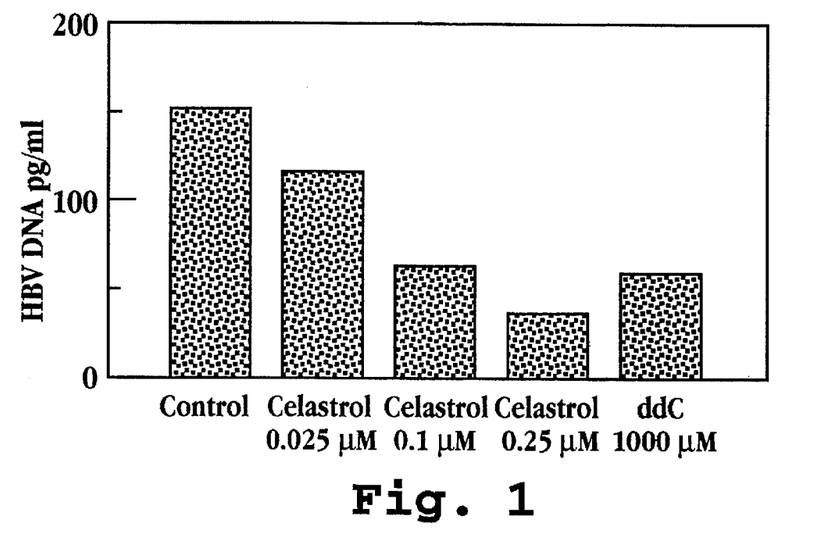
FIG. 1 shows suppression of HBV replication in human hepatoma cells in the absence or presence of celastrol at concentrations of 0, 0.025, 0.1, and 0.25 µM (columns 1 through 4), and in the presence of dideoxycytosine (ddC) at a concentration of 1000 µM (column 5)

As detailed in Example 1, monolayers of hepatoma cells were grown to about 70% confluency, after which celastrol or ddC was added at various concentrations. Secreted virus was assayed by a modification of the slot-blot hybridization method of Marion et al. (1987). The results are shown in FIG. 1.

As can be seen, celastrol is effective to decrease secretion of HBV DNA in a dose-dependent fashion, with half-maximal inhibition occurring at a celastrol concentration of approximately 150 nM (see columns 2 through 4 of figure). Celastrol is significantly more potent than the reference antiviral nucleoside, dideoxycytidine (ddC), which showed inhibition of about 60% at a concentration of 1000 μM (1 mM). Thus, on a mole/mole basis, celastrol appears to be more potent by a factor of about 1,000.

In another study, detailed in Example 2, celastrol was tested for its ability to suppress secretion of HBsAg antigen from human hepatoma cells in a transient transfection assay.

After transfection for 16 hours, transfection medium (1 ml) was replaced with fresh culture medium (1 ml) with or without 1 μM celastrol or 1000 μM ddC. Culture supernatants from the transfected cells were collected every 24 hours for a period of 4 days and were centrifuged prior to storage at −20° C. HBsAg immunoreactivity was determined for culture supernatants using a commercial ELISA assay. The results are shown in FIG. 2.

Figure 2:
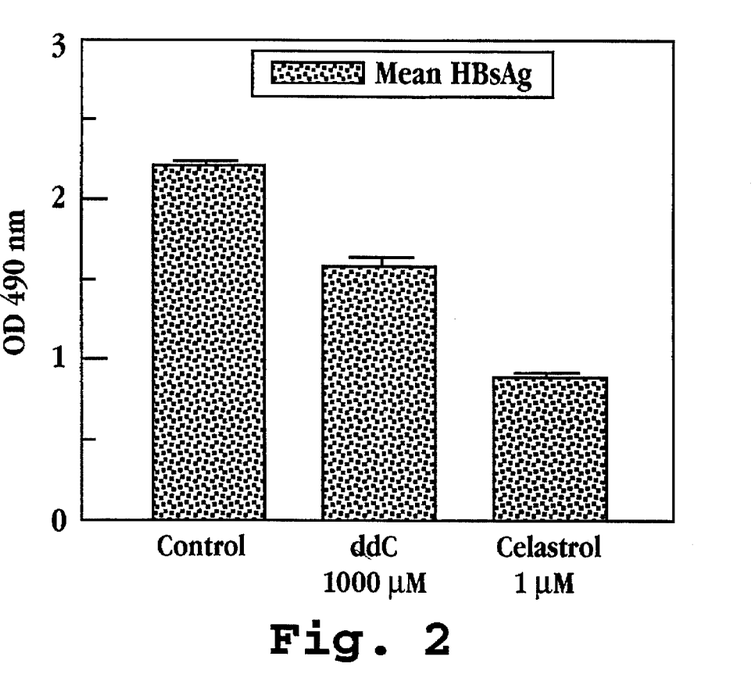
FIG. 2 shows suppression of HBsAg antigen secretion from HuH7 hepatoma cells transiently transfected with HBV DNA following exposure for four days to either no drug (left-hand column), 1000 µM ddC (middle column) or 1 µM celastrol (right-hand column)

FIG. 2 shows that a modest reduction in antigen secretion of about 25% is obtained in the presence of 1000 μM ddC (middle column), relative to the level of secretion in the absence of drug. In contrast, celastrol at a concentration of 1 μM is effective to reduce secretion by greater than 50% relative to the absence of drug, and by almost 50% relative to the level of secretion observed with 1000 μM ddC. Thus, celastrol is more potent the than the reference antiviral compound ddC by a factor of about 1,000.

B. Immunosuppressive Effects

Figure 3:
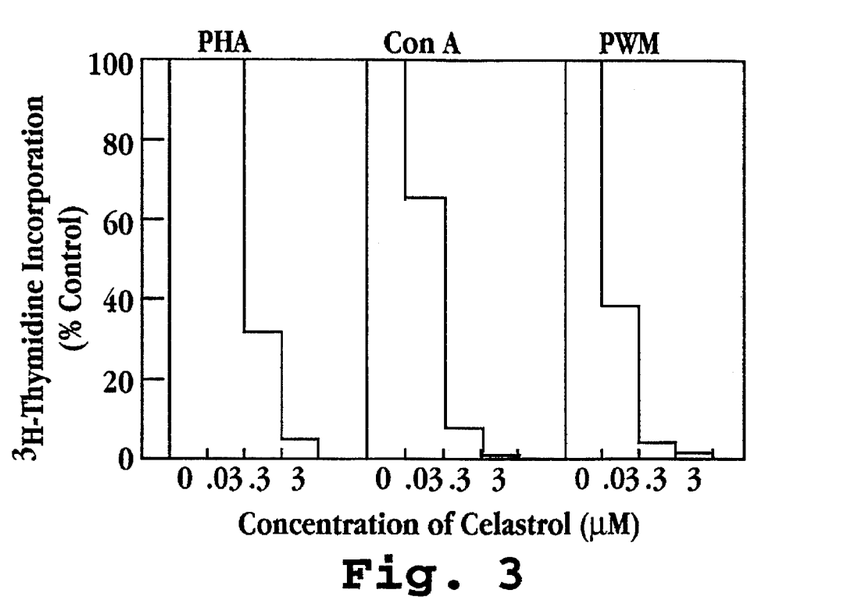
FIG. 3 illustrates the suppressive effects of celastrol on proliferative responses of lymphocytes to the mitogens phytohemagglutinin (PHA, 3A), concanavalin A (Con A, 3B), and pokeweed mitogen (PWM, 3C), as measured by $^3$H-thymidine incorporation.

In addition to inhibiting HBV replication, the compounds of the invention also afford immunosuppressive effects which are useful, for example, in moderating the immune response against HBV. In the assay described in Example 3, human peripheral blood mononuclear cell and mouse spleen cell cultures were set up according to the methods of Dumont et al. (1995), in the presence of the mitogens phytohemagglutinin (PHA), concanavalin A (Con A), or pokeweed mitogen, to induce cell proliferation. Cultures were incubated with mitogen in the presence of celastrol at concentrations of 0, 0.03, 0.3, and 3 μM for 72 h at 37° C. The cells were then pulsed with tritiated thymidine for 6 h before harvesting, after which the levels of tritium uptake were determined. The results are shown in FIG. 3.

As can be seen, celastrol is effective to suppress, in a dose-dependent fashion, proliferation of the lymphocytes in response to all the mitogens tested. The concentrations of drug required to suppress proliferation by 50% are in the range of about 20 to 80 nM for all the mitogens tested.

C. Suppression of the Production of TNF-$\alpha$ and IL-1$\beta$

Figure 4A:
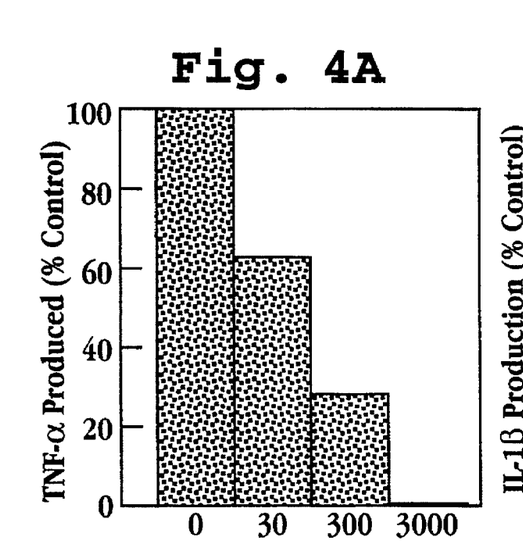
FIGS. 4A–4B illustrate the suppressive effects of celastrol on the production of TNF-α and IL-1β in human monocytes stimulated by bacterial lipopolysaccharide (LPS)
Figure 4B:
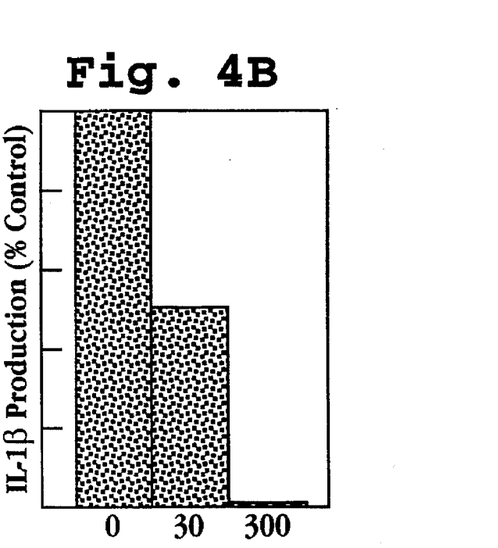

TNF-$\alpha$ and IL-1$\beta$ are produced by monocytes and macrophages stimulated by bacterial lipopolysaccharides, by activated lymphocytes, or in other ways. These two cytokines play a role in the pathogenesis of inflammation. As shown in FIGS. 4A and 4B, celastrol, in nanomolar concentrations, is a potent inhibitor of the production of TNF-$\alpha$ and IL-1$\beta$ by human monocytes stimulated with LPS.

Celastrol also inhibits the production of these cytokines by human lung macrophages, as shown in Example 5. Human lung macrophages were recovered by fiberoptic bronchoscopy from patients and cultured in RPMI containing 2% fetal calf serum with or without drug (celastrol). Celastrol was added to the cultures at concentrations of 0, 20, 50, 100, and 200 nM. One hour later, lipopolysaccharide (LPS, ≈500 mg/ml) was added to stimulate the production of cytokines. Following 24 hr incubation, culture media were recovered, and TNF-$\alpha$ and IL-1$\beta$ concentrations were determined by immunoassay.

Figure 5:
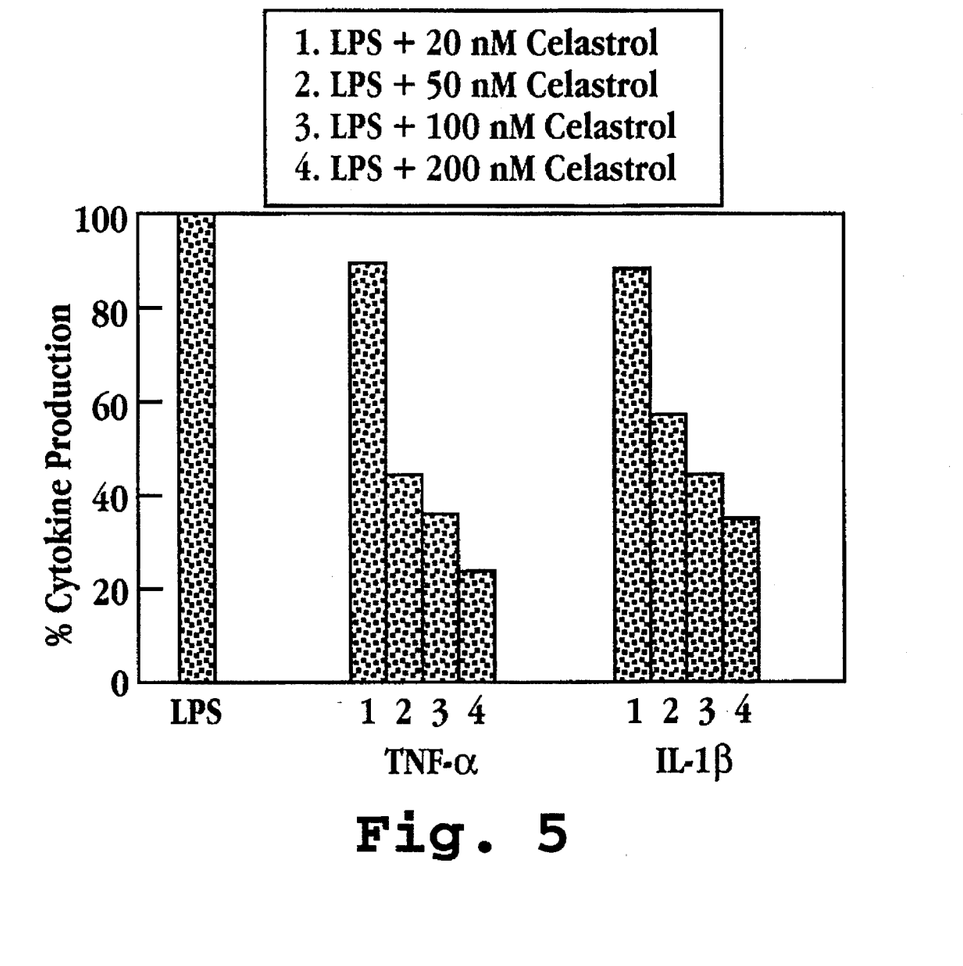
FIG. 5 shows inhibition of LPS-stimulated cytokine production in human lung macrophages in the absence of drug (left column), and in the presence of celastrol at concentrations of 20, 50, 100, and 200 nM, for TNF production (middle four columns) and IL-1β (four columns on right).

With reference to FIG. 5, it can be seen that celastrol strongly inhibits the production of both TNF-$\alpha$ and IL-1$\beta$ in a dose-dependent manner, with concentrations effecting half-maximal inhibition of about 50 nM for both cytokines measured.

D. Characterization of Acetylcelastrol and Pristimerin With Respect to Inhibition of Cytokine Production Because celastrol is relatively unstable in the presence of oxygen, it is preferable in a pharmaceutical formulation to use a prodrug (i.e., diester) having greater stability.

In the study described in Example 6, the inhibitory activities of celastrol, acetylcelastrol, and pristimerin against IL-6 production by human lung macrophages were determined using an indirect assay based on rat hepatoma cells. In response to exogenous IL-6, the hepatoma cells produce a number of acute-phase proteins at levels proportional to those of IL-6 in the culture medium.

In brief, rat hepatoma H35 cells were cultured with supernatants from human lung macrophages which had been incubated for 24 hours with LPS alone, or with LPS plus drug (celastrol, acetylcelastrol, and pristimerin) at concentrations of 50 and 100 nM. Following this incubation, the levels of the following acute-phase proteins were measured, as indicators of prior IL-6 production by the human lung macrophages: C3 component of complement (CC3), fibrinogen (FBG), and alpha-2-macroglobulin (A2M).

As shown in Table 1 (see Example 6), 50 nM celastrol affords modest reductions in secreted protein levels, and, with the exception of CC3, provides greater reductions when the celastrol concentration is increased to 100 nM. Surprisingly, significantly higher levels of inhibition are seen with acetylcelastrol and pristimerin. At a concentration of 100 nM, pristimerin inhibits acute-phase protein secretion by 31–38%, and even greater inhibition (42–73%) is seen with acetylcelastrol.

These results indicate that the three compounds tested are all taken up by lung macrophages, and that the derivatives acetylcelastrol and pristimerin appear to be taken up or retained more efficiently than celastrol itself. It is clear that ester groups are not only innocuous with respect to cytokine inhibition activity, but in fact appear to enhance the activity. Furthermore, the data indicate that following uptake, the ester substituents are cleaved by cellular esterases to produce the active form, celastrol. The data may also reflect acylation of cellular targets by the ester compounds, leading to the inactivation of receptors or signal transduction pathways that mediate cytokine production. Overall, the data establish that the mono and diester compounds are capable of producing anti-inflammatory effects.

E. Inhibition of Nitric Oxide production by Alveolar Macrophages

According to another feature of the invention, compounds in accordance with the invention are effective to reduce nitric oxide production by activated lung macrophages. Nitric oxide production is problematic because it can combine with superoxide to produce the powerful oxidant peroxynitrite, leading to nitration of tyrosine residues in proteins, and cell damage. In patients afflicted with respiratory distress syndrome, sepsis, or pneumonia, nitrated tyrosine residues are observed.

Example 7 describes a study in which celastrol, acetylcelastrol, and pristimerin were tested for inhibitory activity against the production of nitric oxide by rat alveolar macrophages. With reference to Table 2, acetylcelastrol and pristimerin at concentrations of 20 nM are effective to reduce nitric oxide production by 23 and 32%, respectively. In contrast, celastrol does not show inhibitory activity at the concentration tested. The results indicate that derivatives of celastrol are preferred to achieve superior inhibitory effects, possibly because of superior uptake and/or retention of the derivatives.

IV. Treatment Method

In one embodiment, the treatment method of the invention is directed toward treatment of a mammalian subject infected with HBV, wherein the subject is administered a therapeutically effective amount of a compound having the structure shown at Formula 1 above.

The presence of HBV infection in the subject may be detected and monitored by any suitable method known in the biochemical art. Typically, HBV infection can be detected by immunoassay of a body fluid, the immunoassay being specific for HBV-derived antigens or circulating antibodies. Any suitable body fluid may be used for the assay, including blood, urine, saliva, and semen, for example. Typically, the tested body fluid is blood.

The HBV-specific analyte which is detected may be any biological species, e.g., protein, produced by the HBV virus and having diagnostic utility. Exemplary antigens include the hepatitis B surface antigen ($HB_sAg$), the hepatitis B core antigen ($HB_cg$), and the cryptic hepatitis $B_o$ antigen ($HB_cg$), as well as the protein kinase and DNA polymerase associated with the virus.

Alternatively, the HBV-specific analyte may be a circulating antibody specific against an HBV antigen. Exemplary circulating antibodies which may be useful include anti-$HB_s$, anti-$HB_c$, and anti-$HB_o$ antibodies of the IgM and/or IgG class. Diagnostic methods based on such analytes are described, for example, in Wilson et al. (1991, e.g., Chap. 52; Belshe, 1991).

In another embodiment, HBV is detected on the basis of the presence of viral DNA in a body fluid or tissue of the subject, as determined using PCR or hybridization techniques and virus-specific probes. Examination and assay of liver biopsies are also contemplated.

Upon detection of HBV in the subject, the subject is administered a therapeutically effective amount of a compound of the invention to inhibit replication of the virus. Administration is continued over a time, e.g., several weeks to several months, sufficient to reduce the level of viral products to a selected level. Administration may be continued even after viral antigen has been eliminated. Decisions as to whether therapy should continue may also be made based on the levels of other indicators of liver function, such as serum aminotransferase and bilirubin.

The compound of the invention may be administered by oral or parenteral administration, such as intravenous administration. For oral administration, the compound may be given in tablet or capsule form, at a preferred dose of 0.1 to 10 mg/kg body weight per day. The dose may be increased or decreased appropriately depending on the response of the patient and patient tolerance. It will be appreciated that the compounds of the invention may be administered with other therapeutic drugs as appropriate to best maintain the patient's health.

The compounds of the invention are also useful in treating a number of other disease conditions, particularly when the R1 and R2 groups both give rise to ester groups. According to an important feature of the invention, the diester compounds of the invention can impart improved stability (e.g., against oxidation, by the presence of an ester moiety at R1), which facilitates pharmaceutical formulation, as well as improved cellular uptake or retention, relative to unmodified celastrol. Upon uptake in cells, the ester groups may be cleaved by cellular esterases to produce free celastrol, which may be the more active drug form. The compounds may also act through an acylation mechanism, where a nucleophilic group from an enzyme or other protein becomes acylated following attack on an ester moiety at R1 or R2.

The compounds of the invention are also useful in compositions and methods for treating a variety of other medical conditions. For treating Crohn's disease or ulcerative colitis, the compound is administered orally as above to alleviate the disease symptoms.

The diester compounds are also applicable to autoimmune diseases, such as nephritis, rheumatoid arthritis, systemic lupus erythematosus, autoimmune diabetes mellitus and multiple sclerosis. In the treatment method, the patient is given the compound on a periodic basis, e.g., 2–7 times per week at a dosage level sufficient to reduce symptoms and improve patient comfort. Use in conjunction with organ and cellular transplants is also contemplated, to inhibit transplant rejection, and to treat graft-versus-host disease.

The compounds of the invention are also useful for treating septic or traumatic shock. The compound is administered intravenously, preferably in a liposomal or other formulation targeted to macrophages. Administration should be concomitant with fluid replacement and other measures to reverse or arrest hypotension.

In another aspect, the compounds are useful in protecting selected tissues from damage due to the effects of ionizing radiation. Where the tissues are in or near the lungs, the compound is administered in a pharmaceutically acceptable form by inhalation. Where the tissues are part of the intestinal tract, the compound is administered orally as above.

In the case of the administration of an anthracycline drug in the treatment of cancer, the compounds may be coadministered with the drug to alleviate the oxidative effects of the latter on the lining of the intestinal tract. In the case of bleomycin administration, the compounds of the invention may be administered as an inhalant to alleviate potential tissue damage and fibrosis in the lungs.

The invention also includes a method of inhibiting fibrogenesis in the peritoneal or pelvic cavity of a mammalian subject. In the method, the subject is administered a therapeutically effective amount of a compound in accordance with Formula 1, wherein the drug is administered by injection into the peritoneal or pelvic cavity. Where the patient has undergone abdominal surgery, the compound of the invention may be administered in the form of a matrix which is placed (e.g., attached by suture) at or near the site of potential fibrogenesis, under conditions effective to release the compound gradually over time.

The following examples illustrate but are not intended in way to limit the invention.

EXAMPLE 1

Suppression of HBV Replication in Hepatoma Cells

In this study, cells from the 2.2.15 cell line were used, generated by stable transfection of HepG2 cells (Price et al., 1989). Monolayer cultures of the 2.2.15 cells secrete infectious virus into the culture fluid upon reaching confluence.

Monolayer cultures in 96-well plates were grown to about 70% confluency, after which the test drug (celastrol or ddC) was added at various concentrations. The celastrol concentrations tested were 0.025, 0.1, and 0.25 µM; ddC was tested at a concentration of 1000 µM. Media were changed daily, and the supernatants collected every other day. Secreted virus was assayed by a modification of the slot-blot hybridization method described by Marion et al. (1987).

In brief, a slot-blot apparatus was presoaked with denatured salmon sperm DNA, 10 µg/ml. Supernatant fluid (200 µL) was denatured with 20 µl 1M NaOH for 5 min., neutralized with 30 µl 7.5 m NH₄Ac, and then applied to a nylon membrane pre-moistened with 1M NH₄Ac. Excess liquid in the slots was wicked through the membrane, and the DNA was then membrane-linked using a UV "STRATALINKER" 1800 (from Stratagene). The membrane was incubated at 42° C. in Denhardt's solution in 50% formamide supplemented with denatured salmon sperm (100 µg/ml), 1% glycine and 1% sodium dodecyl sulfate.

Hybridization was done by standard methods, using HBV DNA purified from a recombinant plasmid. Controls on each blot included 10 µl of 0, 1, 10, and 100 ng/ml HBV DNA mixed with salmon sperm DNA (1 mg/ml). These were denatured, neutralized, and applied to the nylon fiber.

Autoradiograms exposed to the hybridization blots were scanned with a Helena scanning densitometer. The integrations associated with each slot were converted to HBV DNA in units of pg/ml using a curve derived from known amounts of blotted HBV DNA.

The results of a representative experiment are shown in FIG. 1. As can be seen, celastrol was effective to decrease secretion of HBV DNA in a dose-dependent fashion. With reference to the second, third, and fourth columns of FIG. 1, the concentration of celastrol suppressing HBV replication by 50% was approximately 150 nM. With reference to the fifth column of the figure, which shows the level of suppression obtained with 1000 µM ddC, it can be seen that celastrol is more potent than ddC, on a molar basis by a factor of about 1,000.

EXAMPLE 2

MBV Transfection Assay

Plasmids. The hepatitis B virus genome used to transfect HuH7 cells was a tandem dimer of the adw subtype (Siddiqui, et al., 1981) inserted into the EcoRI site of the pGEM-4 plasmid (Promega, Madison, Wis.).

Cell Culture and Transfections. The human hepatoma cell line HuH7 was grown in RPMI 1640 and Dulbecco's modified Eagle medium (1:1) containing 10% fetal bovine serum. Cells were seeded onto 12-well plates and were transfected after a 24 hour growth period using a modified calcium phosphate co-precipitation method (MBS transfection kit, Stratagene, LaJolla, Calif.). After 16 hours, the transfection medium (1 ml) was replaced with fresh culture medium (1 ml) with or without 1 µM celastrol. Culture supernatants from the transfected cells were collected every 24 hours for a period of 4 days and were centrifuged prior to storage at −20° C.

Isolation and Analysis of HBV Nucleocapsid DNA. Cytoplasmic HBV nucleocapsids were isolated from transfected cells after 4 days by PEG precipitation, and viral nucleic acid was prepared as previously described (Pugh, et al., 1988). For Southern analysis, viral DNA samples were subjected to 1.5% agarose gel electrophoresis, transferred to a nylon membrane, and hybridized to radiolabeled HBV DNA (Sambrook, et al., 1989). For quantitation of HBV DNA, viral DNA samples were applied directly to a nylon membrane using a slot blotter. The membrane was then hybridized to radiolabeled HBV DNA as in the Southern protocol. Quantitation of the radiolabeled probe DNA in each slot was performed using phosphoimaging and comparison with a standard curve of slots containing known amounts of HBV DNA.

HBsAg ELISA Assay. HBsAg immunoreactivity was determined in culture supernatants using the "AUSZME MONOCLONAL HBsAg KIT" (Abbott Laboratories, N. Chicago, Ill.) according to the manufacturer's protocol, with absorbance values (AU) measured at 490 nm. The cell supernatants were diluted 1:40 prior to assay.

The results are given in FIG. 2, which shows the relative levels of HBsAg antigen secreted by the HuH7 cells which had been transiently transfected with HBV DNA. The left-hand column shows the level of HBsAg antigen secreted in the absence of celastrol (2.2 AU). A modest reduction in secretion was obtained with 1 mM ddC, as seen from the middle column (1.6 AU). In contrast, with reference to the right-hand column of FIG. 2, celastrol at a concentration of 1 µM was effective to reduce secretion by greater than 50% (0.85 AU), relative to the absence of drug, and by almost 50% relative to the secretion level observed with 1000 µM ddC.

EXAMPLE 3

Suppression of Lymphocyte Proliferation

Human peripheral blood mononuclear cell and mouse spleen cell cultures were set up in 96-well Costar plates following the procedures described in Dumont et al. (1995). Three groups of wells were prepared containing phytohemagglutinin (PHA), concanavalin A (Con A), or pokeweed mitogen to induce cell proliferation. Cultures were incubated with mitogens with celastrol concentrations of 0 (controls), 0.03, 0.3, and 3 µM for 72 h at 37° C. The cells were then pulsed with 0.5 µCi of tritiated thymidine per well for 6 h before harvesting, after which the levels of tritium uptake were determined.

The results are shown in FIG. 3. As can be seen, celastrol was effective to suppress, in a dose-dependent fashion, proliferation of the lymphocytes in response to all the mitogens tested. The concentrations of drug required to suppress proliferation by 50% were in the range of about 20 to 80 nM.

EXAMPLE 4

Suppression of TNF-α and IL-1β Production

Cultured human peripheral blood mononuclear cells (PBMCs) enriched in monocytes were stimulated with lipopolysaccharide (20 µg/ml) in the presence and absence of celastrol at concentrations of 0, 30, 300, and 3000 nM. After overnight incubation, the cells were collected and lysed, and the concentrations of TNF-α and IL-1β were measured by ELISA. The results are shown in FIGS. 2A and 2B.

As can be seen from FIG. 2A, celastrol showed dose-dependent inhibition of TNF-α production, with half-maximal inhibition at a celastrol concentration of about 70 nM. The results for IL-1β (FIG. 2B) were similar, with half-maximal inhibition occurring at a celastrol concentration of about 30 nM.

EXAMPLE 5

Inhibition of Cytokine production in Human Lung Macrophages

Human lung macrophages were recovered by fiberoptic bronchoscopy from patients examined for diagnostic purposes following the guidelines of the American Thoracic Society (1985). The macrophages were collected in sterile phosphate-buffered saline, centrifuged, suspended in RPMI medium containing 8% fetal calf serum, to a concentration of $10^6$ cells per ml, and distributed into six 24-well plates. Following incubation at 37° C. for 2 hr in an atmosphere equilibrated with 5% $CO_2$, non-adherent cells were removed and the attached cells were incubated for a further 40 hr under the same conditions. The media were then replaced with RPMI containing 2% fetal calf serum with or without drug (celastrol). Drug was added 1 hour before LPS. The drug concentrations were 0, 20, 50, 100, and 200 nM. Lipopolysaccharide (LPS from E. coli 026-86, Sigma, St. Louis, Mo., final concentration ≈500 mg/ml) was used to stimulate the production of cytokines. Following 24 hr incubation, culture media were recovered, and TNF-α and IL-1β concentrations were determined by immunoassay kits (Genzyme, Cambridge, Mass.). The results are shown in FIG. 5, assuming a value of 100% stimulation for LPS alone. The concentrations of celastrol which inhibit cytokine production half-maximally are in the range of 50 to 100 nM.

EXAMPLE 6

Suppression of Cytokine Synthesis by Celastrol Derivatives

In this study, the inhibitory activities of celastrol, acetylcelastrol, and pristimerin on IL-6 production by human lung macrophages were measured indirectly using rat hepatoma H35 cells. The latter produce a number of acute-phase proteins in response to the inducing cytokine IL-6, which can be measured as an indication of IL-6 levels in the culture medium.

Rat hepatoma H35 cells were cultured with supernatants from human macrophages which had been incubated for 24 hours with LPS alone, LPS plus celastrol (50 and 100 nM), LPS plus acetylcelastrol (50 and 100 nM), and LPS plus pristimerin (50 and 100 nM). The levels of selected acute-phase proteins were then measured: C3 component of complement (CC3), fibrinogen (FBG), and alpha-2-macroglobulin (A2M). The results are shown in Table 1 below, with LPS-stimulated protein synthesis assumed as 100%.

TABLE 1

|  | Relative Protein Synthesis | | |
| --- | --- | --- | --- |
| Additives | CC3 | FBG | A2M |
| LPS | 100 | 100 | 100 |
| LPS + CE (50 nM) | 92 | 94 | 87 |
| LPS + CE (100 nM) | 93 | 82 | 61 |
| LPS + ACE (50 nM) | 76 | 83 | 63 |
| LPS + ACE (100 nM) | 58 | 55 | 27 |
| LPS + PRI (50 nM) | 88 | 94 | 100 |
| LPS + PRI (100 nM) | 63 | 69 | 62 |

As seen, both acetylcelastrol and pristimerin inhibit cytokine synthesis, and their activities are more potent than that of celastrol.

EXAMPLE 7

Inhibition of LPS-Induced Nitric Oxide Production

Rat alveolar macrophages were recovered from the lungs of Lewis rats by washing with ice-cold sterile phosphate-buffered saline, and then cultured and stimulated with LPS as described with respect to the human alveolar macrophages in Example 5. Celastrol (CE), acetyl celastrol (ACE), and pristimerin (PRI) were tested at a concentration of 20 nM. The macrophages were incubated in the presence of LPS and drug for 16 hours prior to assay.

To assay nitric oxide (NO) production, rat culture media were centrifuged, and samples (80 µl) were transferred to a microtiter plate. Eighty microliters of Griess reagent (1% sulfanilamide (0.1% naphthyl ethylenediamine dihydrochloride in 2.5% $H_3PO_4$) was added to each well. After 10 min at room temperature, the absorbance was read using a 540 nm filter. Dilutions of sodium nitrite in water were used as standard (Ding et al., 1988). The results are shown in Table 2 below.

TABLE 2

| Additives | [NO] (μM) | % [NO] |
|---|---|---|
| LPS | 32.7 | 100 |
| LPS + CE (20 nM) | 33.1 | 101 |
| LPS + ACE (20 nM) | 25.3 | 77 |
| LPS + PRI (20 nM) | 22.2 | 68 |

Acetylcelatrol and pristimerin both have significant activity at 20 nM concentration whereas celastrol does not. High concentrations of all the drugs suppress NO production almost completely (data not shown).

EXAMPLE 8

Oral Formulation #1

This example illustrates representative pharmaceutical formulations for oral administration.

| INGREDIENTS | QUANTITY PER TABLET (MG) |
|---|---|
| Formula 1 compound | 400 |
| Cornstarch | 50 |
| Lactose | 145 |
| Magnesium stearate | 5 |

The above ingredients are mixed and then pressed into single scored tablets.

Oral Formulation #2

| INGREDIENTS | QUANTITY PER TABLET (MG) |
|---|---|
| Formula 1 compound | 200 |
| Lactose, spray dried | 148 |
| Magnesium stearate | 2 |

The above ingredients are mixed and introduced into a hard-shell gelatin capsule.

Oral Formulation #3

A liquid suspension for oral administration in accordance with the invention is as follows:

| INGREDIENTS | QUANTITY |
|---|---|
| Formula 1 compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K* | 1.0 g |
| Flavoring | 0.035 ml |
| Colorings | 0.5 mg |
| Distilled water | 0.5 mg |

*Vanderbilt Co.

While the invention has been described with reference to specific methods and embodiments, it will be appreciated that various modifications may be made without departing from the invention.

It is claimed:

1. A method of inhibiting hepatitis B infection in a mammalian subject, comprising administering to the subject a therapeutically effective amount of a compound having the formula:

wherein $R_1$ is selected from the group consisting of H and lower alkanoyl, and $R_2$ is separately selected from the group consisting of H and lower alkyl.

2. The method of claim 1, wherein $R_1$ and $R_2$ are H.

3. The method of claim 1, wherein $R_1$ is acetyl, and $R_2$ is ethyl.

4. The method of claim 1, wherein $R_1$ is H and $R_2$ is ethyl.

5. The method of claim 1, wherein $R_1$ is acetyl and $R_2$ is H.

6. The method of claim 1, wherein the compound is administered orally.

* * * * *